(12) United States Patent
Hercouet et al.

(10) Patent No.: US 9,017,424 B2
(45) Date of Patent: *Apr. 28, 2015

(54) PROCESS FOR LIGHTENING KERATIN MATERIALS USING AN EMULSION COMPRISING AN ALKALINE AGENT AND AN OXIDIZING COMPOSITION

(75) Inventors: Leïla Hercouet, Neuilly Plaisance (FR); Anne-Laure Bernard, Antony (FR); Dominique Bordeaux, Soisy sur Seine (FR)

(73) Assignee: L'Oreal, Paris (FR)

( * ) Notice: Subject to any disclaimer, the term of this patent is extended or adjusted under 35 U.S.C. 154(b) by 501 days.

This patent is subject to a terminal disclaimer.

(21) Appl. No.: 12/642,412

(22) Filed: Dec. 18, 2009

(65) Prior Publication Data

US 2010/0166688 A1    Jul. 1, 2010

Related U.S. Application Data

(60) Provisional application No. 61/150,923, filed on Feb. 9, 2009.

(30) Foreign Application Priority Data

Dec. 19, 2008 (FR) ...................... 08 58890

(51) Int. Cl.
A61K 8/30 (2006.01)
A61Q 5/08 (2006.01)
A61K 8/31 (2006.01)
A61K 8/41 (2006.01)
A61K 8/86 (2006.01)
A61K 8/37 (2006.01)
A61K 8/06 (2006.01)

(52) U.S. Cl.
CPC ... *A61Q 5/08* (2013.01); *A61K 8/31* (2013.01); *A61K 8/41* (2013.01); *A61K 8/86* (2013.01); *A61K 2800/88* (2013.01); *A61K 8/37* (2013.01); *A61K 8/062* (2013.01)

(58) Field of Classification Search
USPC ...................... 252/186.28; 424/401
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,377,250 A * | 4/1968 | Hansen ...................... | 424/70.17 |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 4,845,293 A | 7/1989 | Junino et al. | |
| 5,021,066 A | 6/1991 | Aeby et al. | |
| 5,259,849 A | 11/1993 | Grollier et al. | |
| 5,364,414 A | 11/1994 | Lang et al. | |
| 5,575,948 A * | 11/1996 | Petchul et al. ........... | 252/186.28 |
| 5,585,104 A * | 12/1996 | Ha et al. ........................ | 424/401 |
| 5,817,155 A | 10/1998 | Yasuda et al. | |
| 6,010,541 A | 1/2000 | De La Mettrie | |
| 6,074,439 A | 6/2000 | De La Mettrie et al. | |
| 6,129,770 A | 10/2000 | Deutz et al. | |
| 6,156,713 A | 12/2000 | Chopra et al. | |
| 6,165,444 A | 12/2000 | Dubief et al. | |
| 6,190,421 B1 | 2/2001 | Rondeau et al. | |
| 6,206,935 B1 | 3/2001 | Onitsuka et al. | |
| 6,238,653 B1 | 5/2001 | Narasimhan et al. | |
| 6,251,378 B1 | 6/2001 | Laurent et al. | |
| 6,260,556 B1 | 7/2001 | Legrand et al. | |
| 6,277,154 B1 | 8/2001 | Lorenz | |
| 6,277,155 B1 | 8/2001 | De La Mettrie et al. | |
| 6,365,136 B1 | 4/2002 | Lauscher et al. | |
| 6,423,100 B1 | 7/2002 | Lang et al. | |
| 6,447,552 B1 | 9/2002 | Golinski | |
| 6,645,258 B2 | 11/2003 | Vidal et al. | |
| 6,660,045 B1 | 12/2003 | Hoeffkes et al. | |
| 6,695,887 B2 | 2/2004 | Cottard et al. | |
| 6,800,098 B1 | 10/2004 | Allard et al. | |

(Continued)

FOREIGN PATENT DOCUMENTS

CA   1 268 421   5/1990
CA   2 573 567   3/2006

(Continued)

OTHER PUBLICATIONS

French Search Report for FR 0858890, dated Sep. 21, 2009.

(Continued)

*Primary Examiner* — Walter Webb
(74) *Attorney, Agent, or Firm* — The Marbury Law Group, PLLC

(57) ABSTRACT

The present disclosure therefore relates to a method for lightening keratin materials, in which the following are used: (a) a direct emulsion (A) comprising at least one fatty substance in an amount greater than 25% by weight, such as greater than 50%, at least one surfactant; at least one alkaline agent and an amount of water greater than 5% by weight, of the total weight of the emulsion, (b) a composition (B) comprising at least one oxidizing agent. It also relates to a multi-compartment device comprising, in one compartment, an emulsion (A), in another compartment a composition (B) comprising at least one oxidizing agent.

16 Claims, No Drawings

(56) References Cited

U.S. PATENT DOCUMENTS

| | | |
|---|---|---|
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |
| 7,575,605 B2 | 8/2009 | Legrand |
| 7,651,533 B2 | 1/2010 | Legrand |
| 7,651,536 B2 | 1/2010 | Cottard et al. |
| 7,766,977 B2 | 8/2010 | Cottard |
| 2003/0190297 A1 | 10/2003 | Narasimham et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0208903 A1* | 10/2004 | Robinson et al. ............ 424/401 |
| 2004/0226110 A1 | 11/2004 | LeGrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2005/0283925 A1* | 12/2005 | Glenn et al. ...................... 8/405 |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | Decoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1 | 6/2009 | Brun |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| CH | 507 713 | 7/1971 |
| DE | 20 05 076 | 8/1970 |
| DE | 38 14 356 C2 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 B1 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 A1 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 9-249537 | 9/1997 |
| JP | 10-101537 | 4/1998 |
| JP | 2001-233748 | 8/2001 |
| JP | 2001-302471 | 10/2001 |
| JP | 2003-55174 | 2/2003 |
| JP | 2003-095984 | 4/2003 |
| JP | 2003-238370 | 8/2003 |
| JP | 2004-262886 | 9/2004 |
| JP | 2006-282524 | 10/2006 |

(56) References Cited

FOREIGN PATENT DOCUMENTS

| | | |
|---|---|---|
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 A1 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2008/138844 | 11/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

English language abstract of DE 38 14 356 C2, Jan. 2, 1992.
English language abstract of FR 2 910 309 A1, Jun. 27, 2008.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 20 05 076, dated Aug. 6, 1970.
English language Abstract of DE 38 14 356, dated Sep. 8, 1988.
English language Abstract of DE 43 09 509, dated Sep. 19, 1994.
English language Abstract of EP 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 716 840, dated Nov. 2, 2006.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.

(56) References Cited

OTHER PUBLICATIONS

French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/339,820, dated Jan. 21, 2010.
STIC Search Report for U.S. Appl. No. 12/642,492, dated Jul. 14, 2010.
English translation of Japanese Office Action for counterpart Japanese Patent Application No. 2009-288197, mailed Mar. 31, 2014.

* cited by examiner

PROCESS FOR LIGHTENING KERATIN MATERIALS USING AN EMULSION COMPRISING AN ALKALINE AGENT AND AN OXIDIZING COMPOSITION

This application claims benefit of U.S. Provisional Application No. 61/150,923, filed Feb. 9, 2009. This application also claims benefit of priority under 35 U.S.C. §119 to French Patent Application No. 0858890, filed Dec. 19, 2008.

The present disclosure relates to a method for lightening human keratin materials, for example the hair fibers.

Methods for lightening keratin materials such as human keratin fibers may use an aqueous composition comprising at least one oxidizing agent, under alkaline pH conditions in the vast majority of cases. This oxidizing agent has the role of degrading the melanin of the hair, which, depending on the nature of the oxidizing agent present, may lead to a more or less pronounced lightening of the fibers. For relatively weak lightening, the oxidizing agent is generally hydrogen peroxide. When greater lightening is sought, use may be made of peroxygenated salts, such as persulfates, in the presence of hydrogen peroxide.

One of the difficulties arises from the fact that lightening methods may be performed under alkaline conditions and the alkaline agent most commonly used is aqueous ammonia. The reason that aqueous ammonia may be used is that it allows the pH of the composition to be adjusted to an alkaline pH to enable activation of the oxidizing agent. This agent also may cause swelling of the keratin fiber, with opening of the scales, which promotes the penetration of the oxidizing agent into the fiber, and increases the efficacy of the reaction.

However, this basifying agent may be very volatile, which many users find disagreeable due to the characteristic strong, rather unpleasant odor of ammonia that is given off during the method.

Furthermore, the amount of ammonia given off requires the use of higher contents than may be necessary in order to compensate for this loss. This is not without consequences on the user, who not only remains inconvenienced by the odor, but may also be confronted with greater risks of intolerance, for instance irritation of the scalp such as stinging.

As regards the option of purely and simply replacing all or some of the aqueous ammonia with at least one other standard basifying agent, this may not lead to compositions that are as efficient as those based on aqueous ammonia. For example these basifying agents do not afford sufficient lightening of pigmented fibers in the presence of the oxidizing agent.

One of the objects of the present disclosure is to propose methods for lightening keratin materials, for example keratin fibers such as the hair, which may not have drawbacks of those used with existing compositions, due to the presence of large amounts of aqueous ammonia, while at the same time remaining at least as efficient, as regards the lightening and the homogeneity of said lightening.

These aims and others can be achieved by the present disclosure, one subject of which is therefore a method for lightening keratin materials, in which the following is applied to keratin materials:

(a) a direct emulsion (A) comprising at least one fatty substance other than fatty acids in an amount greater than 25% by weight, at least one surfactant, at least one alkaline agent, and an amount of water greater than 5% by weight, of the total weight of the emulsion; and (b) a composition (B) comprising at least one oxidizing agent.

In certain embodiments, the direct emulsion (A) comprising at least one fatty substance other than fatty acids in an amount greater than 50% by weight relative to the total weight of the emulsion.

The disclosure also relates to a multi-compartment device comprising, in one compartment, an emulsion (A) comprising at least one fatty substance other than fatty acids in an amount greater than 25% by weight at least one surfactant; at least one alkaline agent and an amount of water greater than 5% by weight, of the total weight of the emulsion, and in another compartment a composition (B) comprising at least one oxidizing agent.

In the context of the disclosure, a direct emulsion may be an oil-in-water emulsion.

In the text herein below, and unless otherwise indicated, the limits of a range of values are included in that range.

The keratin materials treated by the method according to the disclosure are, for example, bodily hair, the eyelashes and head hair. The method of the present disclosure makes it possible, for example, to obtain a good level of lightening of these keratin materials such as head hair, without giving off an odor of ammonia, which may be an irritant.

The emulsion (A) may have a water content of less than 50% by weight, such as ranging from 10 to less than 50% by weight relative to the weight of the emulsion.

In addition, according to one embodiment, the direct emulsion (A) does not comprise any direct dye or oxidation dye precursor (bases and couplers) usually used for the dyeing of human keratin fibers. In another embodiment, if the direct emulsion (A) does comprise any direct dye or oxidation dye precursor, their total content does not exceed 0.005% by weight relative to the weight of the water-in-oil emulsion. At such a content, only the emulsion would be dyed, i.e. no dyeing effect on the keratin fibers would be observed.

The oil-in-water emulsion useful in the present disclosure comprises at least one fatty substance.

The term "fatty substance" means an organic compound that is insoluble in water at ordinary temperature (25° C.) and at atmospheric pressure (760 mmHg) (solubility of less than 5%, such as 1% or 0.1%). They present in their structure a chain of at least two siloxane groups or at least one hydrocarbon-based chain comprising at least 6 carbon atoms. In addition, the fatty substances are generally soluble in organic solvents under the same temperature and pressure conditions, for instance chloroform, ethanol, benzene, or decamethylcyclopentasiloxane.

According to the present disclosure, the fatty substances are other than fatty acids.

The fatty substances may be chosen from lower alkanes, fatty alcohols, fatty acid esters, fatty alcohol esters, mineral, plant, animal or synthetic oils, such as non-silicone mineral, plant, animal or synthetic oils, non-silicone waxes, and silicones.

It is recalled that, for the purposes of the disclosure, the fatty alcohols, fatty esters and fatty acids may comprise at least one linear or branched, saturated or unsaturated hydrocarbon-based groups comprising 6 to 30 carbon atoms, which may optionally be substituted, with at least one hydroxyl group (such as 1 to 4). If they are unsaturated, these compounds may comprise one to three conjugated or nonconjugated carbon-carbon double bonds.

As regards lower alkanes, these alkanes comprise from 6 to 16 carbon atoms and are linear or branched, optionally cyclic. By way of example, the alkanes may be chosen from hexane and dodecane, isoparaffins such as isohexadecane and isodecane.

As non-silicone oils that may be used in the composition of the disclosure, examples that may be mentioned include:

hydrocarbon-based oils of animal origin, such as perhydrosqualene;

hydrocarbon-based oils of plant origin, such as liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of more than 16 carbon atoms and of mineral or synthetic origin, such as liquid paraffins, petroleum jelly, liquid petroleum jelly, polydecenes, hydrogenated polyisobutene such as PARLEAM®;

partially hydrocarbon-based fluoro oils; fluoro oils that may also be mentioned include perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols which may be used as fatty substances in the composition of the disclosure include non-alkylenated, saturated or unsaturated, linear or branched and comprise from 6 to 30 carbon atoms such as from 8 to 30 carbon atoms. Mention may be made of cetyl alcohol, stearyl alcohol and the mixture thereof (cetylstearyl alcohol), octyldodecanol, 2-butyloctanol, 2-hexyldecanol, 2-undecylpentadecanol, oleyl alcohol, or linoleyl alcohol.

The non-silicone wax which may be used in the composition of the disclosure may be chosen from carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the disclosure are for example marine waxes such as the product sold by the company Sophim under the reference M82, and polyethylene waxes or polyolefin waxes in general.

Suitable esters include esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters may be greater than or equal to 10.

Among the monoesters, non-limiting examples include dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isonoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still in the context of this embodiment, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra-, or pentahydroxy alcohols may also be used.

The following are non-limiting examples of suitable esters: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is possible to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate, or cetyl octanoate.

The composition may also comprise, as fatty ester, sugar esters and diesters of $C_6$-$C_{30}$ such as $C_{12}$-$C_{22}$ fatty acids. The term "sugar" means oxygen-bearing hydrocarbon-based compounds comprising several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, for example alkyl derivatives, such as methyl derivatives, for instance methylglucose.

The sugar esters of fatty acids may be chosen from esters or mixtures of esters of sugars described previously and of linear or branched, saturated or unsaturated $C_6$-$C_{30}$ such as $C_{12}$-$C_{22}$ fatty acids. If they are unsaturated, these compounds may comprise one to three conjugated or nonconjugated carbon-carbon double bonds.

The esters according to this embodiment may also be chosen from mono-, di, tri-, tetraesters, and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, oleo-palmitate, oleo-stearate, and palmito-stearate mixed esters.

It is possible to use monoesters and diesters such as sucrose, glucose or methylglucose mono- or dioleates, stearates, behenates, oleopalmitates, linoleates, linolenates, and oleostearates.

An example that may be mentioned is the product sold under the name GLUCATE® DO by the company Amerchol, which is a methylglucose dioleate.

Examples of esters or mixtures of esters of sugar and of fatty acid that may also be mentioned include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name RYOTO SUGAR ESTERS, for example referenced B370 and corresponding to sucrose behenate formed from 20% monoester and 80% di-triester-polyester; and the sucrose mono-dipalmito-stearate sold by the company Goldschmidt under the name TEGOSOFT® PSE.

The silicones that may be used in the composition of the present disclosure are volatile or nonvolatile, cyclic, linear or branched silicones, which are unmodified or modified with organic groups, having a viscosity from $5\times10^{-6}$ to 2.5 m$^2$/s at 25° C., such as $1\times10^{-5}$ to 1 m$^2$/s.

The silicones that may be used in accordance with the disclosure may be in the form of oils, waxes, resins, or gums.

The silicone may be chosen from polydialkylsiloxanes, such as polydimethylsiloxanes (PDMS), and organomodified polysiloxanes comprising at least one functional group chosen from poly(oxyalkylene) groups, amino groups, and alkoxy groups.

The organopolysiloxanes are defined in greater detail in Walter Noll's "Chemistry and Technology of Silicones" (1968) Academic Press. They can be volatile or nonvolatile.

When they are volatile, the silicones may be chosen from those having a boiling point ranging from 60° C. to 260° C. In certain embodiments, the silicones may be chosen from (i) cyclic polydialkylsiloxanes comprising from 3 to 7 such as 4 to 5 silicon atoms. These may be, for example, octamethylcyclotetrasiloxane sold under the name VOLATILE SILICONE® 7207 by Union Carbide or SILIBIONE® 70045 V 2 by Rhodia, decamethylcyclopentasiloxane sold under the name VOLATILE SILICONE® 7158 by Union Carbide, and SILIBIONE® 70045 V 5 by Rhodia, and mixtures thereof.

Mention may also be made of cyclocopolymers of the dimethylsiloxane/methylalkylsiloxane type, such as VOLATILE SILICONE® FZ 3109 sold by the company Union Carbide, of formula:

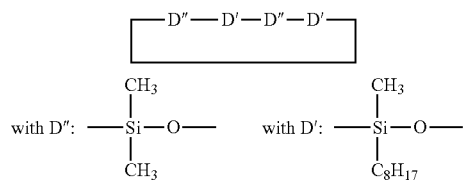

Mention may also be made of mixtures of cyclic polydialkylsiloxanes with organosilicon compounds, such as the mixture of octamethylcyclotetrasiloxane and tetra-trimethylsilylpentaerythritol (50/50) and the mixture of octamethylcyclotetrasiloxane and oxy-1,1'-bis(2,2,2',2',3,3'-hexatrimethylsilyloxy)neopentane.

In additional embodiments, the silicones may be chosen from (ii) linear volatile polydialkylsiloxanes comprising 2 to 9 silicon atoms and having a viscosity of less than or equal to $5\times10^{-6}$ m$^2$/s at 25° C. An example is decamethyltetrasiloxane sold for example under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Nonvolatile polydialkylsiloxanes, polydialkylsiloxane gums and resins, polyorganosiloxanes modified with organofunctional groups above, and mixtures thereof, may be used.

These silicones may be chosen from polydialkylsiloxanes, among which mention may be made of polydimethylsiloxanes comprising trimethylsilyl end groups. The viscosity of the silicones is measured, for example, at 25° C. according to ASTM standard 445 Appendix C.

Among these polydialkylsiloxanes, non-limiting examples include the following commercial products:

the SILBIONE® oils of the 47 and 70 047 series or the MIRASIL® oils sold by Rhodia, for instance the oil 70 047 V 500 000;

the oils of the MIRASIL® series sold by the company Rhodia;

the oils of the 200 series from the company Dow Corning, such as DC200 with a viscosity of 60 000 mm$^2$/s; and the VISCASIL® oils from General Electric and certain oils of the SF series (SF 96, SF 18) from General Electric.

Mention may also be made of polydimethylsiloxanes comprising dimethylsilanol end groups known under the name Dimethiconol (CTFA), such as the oils of the 48 series from the company Rhodia.

In this category of polydialkylsiloxanes, non-limiting examples include the products sold under the names ABIL WAX® 9800 and 9801 by the company Goldschmidt, which are poly($C_1$-$C_{20}$)dialkylsiloxanes.

The silicone gums that can be used in accordance with the disclosure may be polydialkylsiloxanes and such as polydimethylsiloxanes with high number-average molecular masses ranging from 200,000 to 1,000,000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane, and tridecane, or mixtures thereof.

Products that can be used in accordance with the disclosure are mixtures such as:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane; and mixtures of two PDMSs with different viscosities, such as a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5\times10^{-6}$ m$^2$/s. This product may comprise 15% SE 30 gum and 85% SF 96 oil.

The organopolysiloxane resins that can be used in accordance with the disclosure include crosslinked siloxane systems comprising the following units:

$R_2SiO_{2/2}$, $R_3SiO_{1/2}$, $RSiO_{3/2}$ and 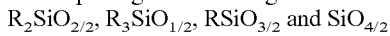

in which R represents a hydrocarbon-based group comprising 1 to 16 carbon atoms. Among these products, R may represent a $C_1$-$C_4$ lower alkyl radical, such as methyl.

Among these resins, mention may be made of the product sold under the name DOW CORNING 593 or those sold under the names SILICONE FLUID SS 4230 and SS 4267 by the company General Electric, which are silicones of dimethyl/trimethyl siloxane structure.

Mention may also be made of the trimethyl siloxysilicate type resins sold for example under the names X22-4914, X21-5034 and X21-5037 by the company Shin-Etsu.

The organomodified silicones that can be used in accordance with the disclosure are silicones as defined above and comprising in their structure at least one organofunctional group attached via a hydrocarbon-based radical.

Besides the silicones described above, the organomodified silicones may be polydiarylsiloxanes, such as polydiphenylsiloxanes, and polyalkylarylsiloxanes functionalized with the organofunctional groups mentioned previously.

The polyalkylarylsiloxanes may be chosen from linear and/or branched polydimethyl/methylphenylsiloxanes and polydimethyl/diphenylsiloxanes with a viscosity of from $1 \times 10^{-5}$ to $5 \times 10^{-2}$ m$^2$/s at 25° C.

Among these polyalkylarylsiloxanes, examples that may be mentioned include the products sold under the following names:
the SILIBIONE® oils of the 70 641 series from Rhodia;
the oils of the RHODOURSIL® 70 633 and 763 series from Rhodia;
the oil DOW CORNING 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, non-limiting examples include polyorganosiloxanes comprising:
polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;
substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, $C_1$-$C_4$ aminoalkyl groups;
alkoxylated groups such as the product sold under the name SILICONE COPOLYMER F-755 by SWS Silicones, and ABIL WAX® 2428, 2434 and 2440 by the company Goldschmidt.

In certain embodiments, the fatty substances are neither oxyalkylenated nor glycerolated.

The fatty substances may be chosen from compounds that are liquid or pasty at room temperature and at atmospheric pressure.

For example, the fatty substance is a compound that is liquid at a temperature of 25° C. and at atmospheric pressure.

The fatty substances may be chosen from lower alkanes, fatty alcohols, fatty acid esters, fatty alcohol esters, oils, such as mineral, plant or synthetic non-silicone oils, and silicones.

According to one embodiment, the fatty substance may be chosen from liquid petroleum jelly, polydecenes, liquid esters of fatty acids or of fatty alcohols, or mixtures thereof; for example, the fatty substance of the composition according to the disclosure may be a non-silicone.

In additional embodiments, alkanes or hydrocarbons and silicones may be chosen as the fatty substance.

The composition according to the disclosure comprises at least 25% of fatty substance relative to the total weight of the composition. For example, in certain embodiments the fatty substance concentration can range from 25% to 80% relative to the total weight of the composition, such as a concentration ranging from 25% to 65%, or a concentration ranging from 30% to 55%.

The emulsion (A) also comprises at least one surfactant.

For example, the surfactant may be chosen from nonionic surfactants and anionic surfactants, such as nonionic surfactants.

The anionic surfactants are for example chosen from the salts (such as alkali metal salts, for example sodium salts, ammonium salts, amine salts, amino alcohol salts or alkaline-earth metal salts such as magnesium salts) of the following compounds:
alkyl sulfates, alkyl ether sulfates, alkylamido ether sulfates, alkylaryl polyether sulfates, monoglyceride sulfates;
alkylsulfonates, alkylamidesulfonates, alkylarylsulfonates, α-olefin sulfonates, paraffin sulfonates;
alkyl phosphates, alkyl ether phosphates;
alkylsulfosuccinates, alkyl ether sulfosuccinates, alkylamidesulfosuccinates; alkylsulfosuccinates;
alkylsulfoacetates;
acylsarcosinates; acylisethionates and N-acyltaurates;
salts of fatty acids such as oleic acid, ricinoleic acid, palmitic acid, or stearic acid, coconut oil acid or hydrogenated coconut oil acid;
alkyl-D-galactoside uronic acid salts;
acyllactylates;
salts of polyoxyalkylenated alkyl ether carboxylic acids, of polyoxyalkylenated alkylaryl ether carboxylic acids or of polyoxyalkylenated alkylamido ether carboxylic acids, for example those comprising from 2 to 50 ethylene oxide groups;
and mixtures thereof.

The alkyl or acyl radical of these various compounds may comprise from 6 to 24 carbon atoms such as from 8 to 22 carbon atoms or from 18 to 22 carbon atoms, and the aryl radical may represent a phenyl or benzyl group.

The nonionic surfactants may be chosen from monooxyalkylenated or polyoxyalkylenated, monoglycerolated or polyglycerolated nonionic surfactants. The oxyalkylene units may be oxyethylene or oxypropylene units, or a combination thereof, such as oxyethylene units.

Examples of oxyalkylenated nonionic surfactants that may be mentioned include:
oxyalkylenated ($C_8$-$C_{24}$)alkylphenols,
saturated or unsaturated, linear or branched, oxyalkylenated $C_8$-$C_{30}$ alcohols,
saturated or unsaturated, linear or branched, oxyalkylenated $C_3$-$C_{30}$ amides,
esters of saturated or unsaturated, linear or branched, $C_8$-$C_{30}$ acids and of polyethylene glycols,
polyoxyethylenated esters of saturated or unsaturated, linear or branched, $C_8$-$C_{30}$ acids and of sorbitol,
saturated or unsaturated, oxyethylenated plant oils, and
condensates of ethylene oxide and/or of propylene oxide, inter alia, alone or as mixtures.

The surfactant may comprise a number of moles of ethylene oxide and/or of propylene oxide ranging from 1 to 50 moles, such as ranging from 2 to 30. In certain embodiments, the nonionic surfactants do not comprise any oxypropylene units.

In accordance with one embodiment of the disclosure, the oxyalkylenated nonionic surfactants may be chosen from oxyethylenated $C_8$-$C_{30}$ alcohols, such as oxyethylenated $C_{18}$-$C_{30}$ alcohols.

Examples of ethoxylated fatty alcohols that may be mentioned include adducts of ethylene oxide with lauryl alcohol, such as those comprising from 9 to 50 oxyethylene groups for example those comprising from 10 to 12 oxyethylene groups (Laureth-10 to Laureth-12 in CTFA names); adducts of ethylene oxide with behenyl alcohol, for example those comprising from 9 to 50 oxyethylene groups (Beheneth-9 to Beheneth-50 in CTFA names), such as 10 oxyethylene groups (Beheneth-10); adducts of ethylene oxide with cetostearyl alcohol (mixture of cetyl alcohol and stearyl alcohol), or those comprising from 10 to 30 oxyethylene groups (Ceteareth-10 to Ceteareth-30 in CTFA names); adducts of ethylene oxide with cetyl alcohol, for example those comprising from 10 to 30 oxyethylene groups (Ceteth-10 to Ceteth-30 in CTFA names); adducts of ethylene oxide with stearyl alcohol, for example those comprising from 10 to 30 oxyethylene groups (Steareth-10 to Steareth-30 in CTFA names); adducts of ethylene oxide with isostearyl alcohol, for example those comprising from 10 to 50 oxyethylene groups (Isosteareth-10 to Isosteareth-50 in CTFA names); and mixtures thereof.

Examples of ethoxylated fatty acids that may be mentioned include the adducts of ethylene oxide with lauric, palmitic, stearic or behenic acid, and mixtures thereof, for example those comprising from 9 to 50 oxyethylene groups, such as PEG-9 to PEG-50 laurates (CTFA names: PEG-9 laurate to PEG-50 laurate); PEG-9 to PEG-50 palmitates (CTFA names: PEG-9 palmitate to PEG-50 palmitate); PEG-9 to PEG-50 stearates (CTFA names: PEG-9 stearate to PEG-50 stearate); PEG-9 to PEG-50 palmitostearates; PEG-9 to PEG-50 behenates (CTFA names: PEG-9 behenate to PEG-50 behenate); and mixtures thereof.

In accordance with one embodiment of the disclosure, the oxyalkylenated nonionic surfactants may be chosen from oxyethylenated $C_{18}$-$C_{30}$ alcohols.

Mixtures of these oxyethylenated derivatives of fatty alcohols and of fatty acids may also be used.

According to one embodiment, the emulsion (A) comprises at least one ethoxylated fatty alcohol, such as at least behenyl alcohol.

As non-limiting examples of monoglycerolated or polyglycerolated nonionic surfactants, monoglycerolated or polyglycerolated $C_8$-$C_{40}$ alcohols may be used.

For example, the monoglycerolated or polyglycerolated $C_8$-$C_{40}$ alcohols correspond to the following formula:

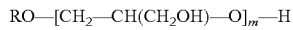

RO—[CH$_2$—CH(CH$_2$OH)—O]$_m$—H in which R represents a linear or branched $C_8$-$C_{40}$ such as $C_8$-$C_{30}$ alkyl or alkenyl radical, and m represents a number ranging from 1 to 30, such as from 1 to 10.

As examples of compounds that are suitable in the context of the disclosure, mention may be made of lauryl alcohol comprising 4 mol of glycerol (INCI name: Polyglyceryl-4 Lauryl Ether), lauryl alcohol containing 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is possible to use the $C_8$/$C_{10}$ alcohol comprising 1 mol of glycerol, the $C_{10}$/$C_{12}$ alcohol comprising 1 mol of glycerol and the $C_{12}$ alcohol comprising 1.5 mol of glycerol.

For example, the surfactant present in the emulsion is a nonionic surfactant having an HLB of 8 to 18. The HLB is the ratio of the hydrophilic part to the lipophilic part in their molecule. This term HLB is well known to those skilled in the art and is described in "The HLB system. A time-saving guide to Emulsifier Selection" (published by ICI Americas Inc; 1984).

The surfactant content in the emulsion (A) may range from 0.1% to 50% by weight relative to the weight of the anhydrous composition, such as a content ranging from 0.5% to 30% by weight.

The emulsion that may be useful in the present disclosure comprises at least one alkaline agent.

The alkaline agent may be chosen from mineral bases, organic amines, and organic amine salts, alone or as a mixture.

Examples of organic amines that may be mentioned are organic amines whose pKb at 25° C. is less than 12, such as less than 10 or less than 6. It should be noted that this is the pKb corresponding to the function of highest basicity.

The organic amine may comprise one or two primary, secondary or tertiary amine functions, and at least one linear or branched $C_1$-$C_8$ alkyl group bearing at least one hydroxyl radical.

Organic amines chosen from alkanolamines such as mono-, di- or trialkanolamines, comprising one to three identical or different $C_1$-$C_4$ hydroxyalkyl radicals, may be suitable for use in the disclosure.

Suitable compounds of this type include monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

The organic amines having the following formula:

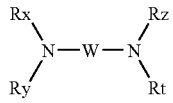

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical, are also suitable for use.

Examples of such amines that may be mentioned include 1,3-diaminopropane, 1,3-diamino-2-propanol, spermine and spermidine.

According to another embodiment of the disclosure, the organic amine is chosen from amino acids.

For example, the amino acids that may be used are of natural or synthetic origin, in L, D or racemic form, and comprise at least one acid function may be chosen more from carboxylic acid, sulfonic acid, phosphonic acid, and phosphoric acid functions. The amino acids may be in their neutral or ionic form.

For example, the amino acids are basic amino acids comprising an additional amine function optionally included in a ring or in a ureido function.

Such basic amino acids may be chosen from those corresponding to formula (I) below:

$$R-CH_2-CH\begin{matrix}NH_2\\ CO_2H\end{matrix} \quad (I)$$

in which R represents a group chosen from:

[imidazole structure]

—$(CH_2)_3NH_2$;
—$(CH_2)_2NH_2$;
—$(CH_2)_2NHCONH_2$; and $$-(CH_2)_2NH-\underset{NH}{\overset{\|}{C}}-NH_2$$

The compounds corresponding to formula (I) include histidine, lysine, arginine, ornithine, and citrulline.

As amino acids that may be used in the present disclosure, non-limiting examples include aspartic acid, glutamic acid, alanine, arginine, ornithine, citrulline, asparagine, carnitine, cysteine, glutamine, lysine, histidine, lysine, isoleucine, leucine, methionine, N-phenylalanine, proline, serine, taurine, threonine, tryptophan, tyrosine, and valine.

According to one embodiment of the disclosure, the organic amine may be chosen from basic amino acids. The amino acids that are for example arginine, lysine, and histidine, or mixtures thereof.

According to another embodiment of the disclosure, the organic amine is chosen from organic amines of heterocyclic type. Besides histidine that has already been mentioned in the amino acids, mention may be made for example of pyridine, piperidine, imidazole, 1,2,4-triazole, tetrazole, and benzimidazole.

According to another embodiment of the disclosure, the organic amine is chosen from amino acid dipeptides. As amino acid dipeptides that may be used in the present disclosure, mention may be made of carnosine, anserine, and baleine.

According to another embodiment of the disclosure, the organic amine is chosen from compounds comprising a guanidine function. As organic amines of this type that may be used in the present disclosure, besides arginine that has already been mentioned as an amino acid, mention may be made of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid.

For example, the organic amine can be an alkanolamine. For example, the organic amine can be chosen from 2-amino-2-methyl-1-propanol and monoethanolamine, or mixtures thereof. In certain embodiments, the organic amine is monoethanolamine.

According to another embodiment, the composition comprises as alkaline agent at least one organic amine, such as at least one alkanolamine. When the composition comprise more than one alkaline agents including an alkanolamine and ammonium hydroxides or their salts, the amount of the organic amine is may be higher than the amount of ammonia.

The alkaline agent may be an organic amine in salt form. For the purposes of the present disclosure, the term "organic amine salt" means organic or mineral salts of an organic amine as described above.

The organic salts may be chosen from the salts of organic acids, such as citrates, lactates, glycolates, gluconates, acetates, propionates, fumarates, oxalates, and tartrates.

The mineral salts may be chosen from hydrohalides (for example hydrochlorides), carbonates, hydrogen carbonates, sulfates, hydrogen phosphates, and phosphates.

For the purposes of the present disclosure, the term "mineral base" means any compound bearing in its structure at least one element from columns 1 to 13 of the Periodic Table of the Elements other than hydrogen, not simultaneously comprising carbon and hydrogen atoms.

According to one embodiment of the disclosure, the mineral base comprises at least one element from columns 1 and 2 of the Periodic Table of the Elements other than hydrogen.

In one embodiment, the mineral base has the following structure:

$$(Z_1^{x-})_m(Z_2^{y+})_n$$

wherein $Z_2$ represents a metal from columns 1 to 13 such as 1 or 2 of the Periodic Table of the Elements, such as sodium or potassium;

$Z_1^{x-}$ represents an anion chosen from the ions $CO_3^{2-}$, $OH^-$, $HCO_3^{2-}$, $SiO_3^{2-}$, $HPO_4^{2-}$, $PO_4^{3-}$, and $B_4O_7^{2-}$, such as from the ions $CO_3^{2-}$, $OH^-$ and $SiO_3^{2-}$;

x represents 1, 2, or 3;

y represents 1, 2, 3, or 4;

m and n represent, independently of each other, 1, 2, 3, or 4;

with $(n)(y)=(m)(x)$.

For example, the mineral base corresponds to the following formula $(Z_1^{x-})_m(Z_2^{y+})_n$, wherein $Z_2$ represents a metal from columns 1 and 2 of the Periodic Table of the Elements; $Z_1^{x-}$ represents an anion chosen from the ions $CO_3^{2-}$, $OH^-$, and $SiO_3^{2-}$, x is 1, y represents 1 or 2, and m and n represent, independently of each other, 1 or 2 with $(n)(y)=(m)(x)$.

As mineral bases that may be used according to the disclosure, non-limiting examples include sodium bicarbonate, potassium carbonate, sodium hydroxide, potassium hydroxide, sodium metasilicates, and potassium metasilicate.

Ammonium salts may also be used as alkaline agent.

The ammonium salts that may be used in the composition B according to the present disclosure are ammonium salts $(NH_4^+)$.

The ammonium salts that may be used in composition B according to the present disclosure may be chosen from the following acid salts: acetate, carbonate, bicarbonate, chloride, citrate, nitrate, nitrite, phosphate, sulfate. The salt may be the carbonate, such as ammonium carbonate.

Generally, the emulsion (A) has an alkaline agent content ranging from 0.1% to 40% by weight relative to the weight of said composition, such as a content ranging from 0.5% to 20% by weight.

The emulsion (A) may be prepared via standard methods of direct emulsion preparation, but also via a PIT method. The principle of emulsification by means of the phase inversion temperature (or PIT) is, in its principle, well known to those skilled in the art; it was described in 1968 by K. Shinoda (J. Chem. Soc. Jpn., 1968, 89, 435). It has been shown that this emulsification technique makes it possible to obtain stable fine emulsions (K. Shinoda and H. Saito, J. Colloid Interface Sci., 1969, 30, 258). This technique was applied in cosmetics as early as 1972 by Mitsui et al. ("Application of the phase-inversion-temperature method to the emulsification of cosmetics"; T. Mitsui, Y. Machida and F. Harusawa, American Cosmet. Perfum., 1972, 87, 33).

The principle of this technique is as follows: a mixture of an aqueous phase and an oily phase is prepared and is brought to a temperature above the PIT temperature, the phase inversion temperature of the system, which is the temperature at which the equilibrium between the hydrophilic and lipophilic properties of the emulsifier(s) used is reached; at elevated temperature, i.e. above the phase inversion temperature (>PIT), the emulsion is of water-in-oil type, and, during its cooling, this emulsion inverts at the phase inversion temperature, to become an emulsion of oil-in-water type, doing so by passing previously through a state of microemulsion. According to this embodiment, the nonionic surfactant has an HLB of between 8 and 18. It may be chosen from ethoxylated fatty alcohols, ethoxylated fatty acids, ethoxylated fatty acid partial glycerides, and polyglycerolated fatty acid triglycerides, and ethoxylated derivatives thereof, and mixtures thereof. Moreover, such an emulsion may have a particle size of less than 4 microns, such as less than 1 μm.

In certain embodiments, it is possible to obtain a PIT emulsion as follows:

1) weighing out in a container all the constituents of the direct emulsion (A);

2) homogenizing the mixture, for example using a Rayneri blender at 350 rpm, while heating by gradually increasing the temperature using a water bath, up to a temperature greater than the phase inversion temperature T1, i.e. until a transparent or translucent phase is obtained (microemulsion zone or lamellar phase), and then until a more viscous phase is obtained, which indicates that the inverse emulsion (W/O) has been obtained;

3) stopping the heating and continuing stirring until the emulsion has cooled to room temperature, passing through the phase inversion temperature T1, i.e. the temperature at which a fine O/W emulsion forms; and 4) when the temperature has fallen below the phase inversion temperature region (T1), adding the optional additives and the heat-sensitive starting materials.

A stable final composition in which the droplets of the lipophilic phase are fine, with sizes from 10 to 200 nm, can be obtained.

In the zone of formation of a microemulsion (translucent mixture), the hydrophilic and hydrophobic interactions are equilibrated since the surfactant has a tendency to form both direct micelles and inverse micelles. By heating beyond this zone, there is formation of a W/O emulsion since the surfactant may favor the formation of a water-in-oil emulsion. Next, on cooling below the phase inversion zone, the emulsion becomes a direct emulsion (O/W).

Emulsification by phase inversion is explained in detail in the publication by T. Fôrster, W. von Rybinski and A. Wadle: Influence of microemulsion phases on the preparation of fine disperse emulsions, Advances in Colloid and Interface Sciences, 58, 119-149, 1995, which is cited herein for reference.

The emulsion (A) may also comprise various adjuvants conventionally used in hair lightening compositions, such as anionic, cationic, nonionic, amphoteric, or zwitterionic polymers or mixtures thereof; mineral thickeners, and fillers such as clays, talc; organic thickeners with, for example, anionic, cationic, nonionic, and amphoteric polymeric associative thickeners; antioxidants; penetrants; sequestrants; fragrances; dispersants; film-forming agents; preserving agents; and opacifiers.

The emulsion (A) may optionally comprise at least one organic solvent. Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, glycerol, diethylene glycol monomethyl ether and monoethyl ether, and also aromatic alcohols, for instance benzyl alcohol or phenoxyethanol, and mixtures thereof.

The method may be performed with a composition (B) comprising at least one oxidizing agent.

The oxidizing agent may be chosen from hydrogen peroxide, urea peroxide, alkali metal bromates or ferricyanides, and peroxygenated salts, for instance alkali metal or alkaline-earth metal persulfates, perborates peracids and precursors thereof, and percarbonates.

This oxidizing agent may constitute hydrogen peroxide, for example as an aqueous solution (aqueous hydrogen peroxide solution), the titre of which may range from 1 to 40 volumes (i.e. 0.3 to 12% of $H_2O_2$) such as from 5 to 40 volumes (i.e. 1.5 to 12% of $H_2O_2$).

As a function of the desired degree of lightening, the oxidizing agent may also comprise an oxidizing agent for example chosen from peroxygenated salts.

The composition (B) is generally an aqueous composition. The term "aqueous composition" means a composition comprising more than 5% by weight of water, for example more than 10% by weight of water, or more than 20% by weight of water.

This composition (B) may also comprise at least one organic solvent as described above. It may also comprise at least one acidifying agent.

Examples of acidifying agents that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

In many embodiments, the pH of the composition (B) is less than 7.

Finally, the composition (B) is in various forms, for instance a solution, an emulsion or a gel.

The method of the disclosure may be used by applying the emulsion (A) and the composition (B) successively and without intermediate rinsing.

According to another embodiment, a composition obtained by extemporaneously mixing, at the time of use, of the emulsion (A) and of the composition (B) is applied to wet or dry keratin materials. According to this embodiment, the weight ratio of the amounts of (A)/(B) and $R_2$ ranges from 0.1 to 10, such as ranging from 0.2 to 2 or ranging from 0.3 to 1.

In addition, independently of the embodiment, the mixture present on the keratin materials (resulting either from the extemporaneous mixing of (A) and (B) or from the partial or total successive application thereof) is left in place for a time, generally from about 1 minute to 1 hour, such as from 5 minutes to 30 minutes.

The temperature during the method is conventionally between room temperature (between 15 and 25° C.) and 80° C. for example between room temperature and 60° C.

After the treatment, the keratin materials are optionally rinsed with water, optionally washed and then rinsed with water, before being dried or left to dry.

In a possible variant of the disclosure, the keratin materials are keratin fibers such as bodily hair, the eyelashes and head hair.

According to one embodiment, the composition of the disclosure obtained from the mixture of the emulsion (A) and the aqueous oxidative agent-comprising composition (B) is such that the amount of fatty substances after mixture is higher than 20%, such as higher than 25%, or higher than 30%.

Finally, the disclosure relates to a multi-compartment device comprising, in a first compartment, an emulsion (A), and, in a second compartment, an aqueous composition (B) comprising at least one oxidizing agent, these compositions having been described previously.

EXAMPLES

The following compositions were prepared:
The emulsion A1 below was prepared according to a phase inversion temperature method (PIT method):
Manufacturing Method:
1. Phase A was heated in a water bath with Rayneri blending (400 rpm). A fluid white emulsion that became translucent at about 68° C. (passing through a microemulsion phase) and thickened above this temperature was obtained.
2. Once the emulsion had thickened, the water bath was removed: the emulsion was allowed to cool with continued stirring.
3. At about 50° C., the Carbopol was introduced.
4. On cooling to room temperature, the ethanol and the monoethanolamine were introduced and the water lost on evaporation (<5%) was readjusted.

A translucent gelled emulsion with droplet sizes <1 µm (viscosity=72 DU M4 by rheomat, pH 11.5) was thus obtained.

| Emulsion A1 | | | |
|---|---|---|---|
| Phase | Name | | g % |
| A | Beheneth-10 | | 6.00 |
|  | Glycerol | | 9.00 |
|  | Ethylhexyl palmitate | | 17.70 |
|  | Liquid petroleum jelly | | 45.00 |
|  | Water | | 16.00 |
| B | Carboxyvinyl polymer synthesized in the ethyl acetate/ cyclohexane mixture (JC: Carbopol 980) | | 0.30 |
| C | Ethanol | | 2.00 |
|  | Monoethanolamine | | 4.00 |

At the time of use, emulsion A1 was mixed weight for weight with an oxidizing aqueous composition (B) comprising a dispersion of fatty alcohols (8%) in water and 12% aqueous hydrogen peroxide solution sold under the name PLATINIUM 20V.

The mixture was then applied to a lock of natural chestnut-brown hair (tone height=4). The bath ratio "mixture/lock" was, respectively, 10/1 (g/g). The leave-on time was 30 minutes at 27° C. After this time, the locks were rinsed and then washed with Elsève multivitamin shampoo. A good level of lightening was obtained, without odor.

Emulsion A2 below was prepared according to a PIT method:
Manufacturing Method:
Phase A was heated in a water bath with Rayneri blending (400 rpm). A fluid white emulsion that became translucent at about 68° C. (passing through a microemulsion phase) and thickened above this temperature was obtained.

Once the emulsion has thickened, the water bath was removed: the emulsion was allowed to cool with continued stirring.

At about 50° C., the poloxamer was introduced.

At room temperature, the ethanol, the monoethanolamine and the potassium bicarbonate predispersed in 5 g of water were introduced, and the water lost on evaporation (<5%) was readjusted.

A translucent gelled emulsion with droplet sizes <1 µm (viscosity=8 DU M4, drop size <1 µm, pH 11.3) was thus obtained.

| Emulsion A2 | | |
|---|---|---|
| Phase | INCI Name | g % |
| A | Beheneth-10 | 6.00 |
|  | Sorbitol | 5.00 |
|  | Liquid petroleum jelly | 60.25 |
|  | Water | 10.00 |
| B | Ethanol | 2.00 |
|  | Poloxamer 184 | 5.00 |
|  | Potassium bicarbonate | 1.75 |
|  | Water | 5.00 |
|  | Monoethanolamine | 5.00 |

At the time of use, 1 weight of emulsion A2 was mixed with 1.5 weights of an oxidizing aqueous composition (B2) comprising a dispersion of fatty alcohols (8%) in water and 12% aqueous hydrogen peroxide solution: PLATINIUM 20V.

The mixture was then applied to a lock of natural chestnut-brown hair (tone height=4). The bath ratio "mixture/lock" was, respectively, 10/1 (g/g). The leave-on time was 30 minutes at 27° C. After this time, the locks were rinsed and then washed with Elsève multivitamin shampoo.

A good level of lightening was obtained, without odor.

Comparative Example

The following aqueous ammonia-based composition was prepared:

|  | g % | |
|---|---|---|
| Oleyl alcohol polyglycerolated with 2 mol of glycerol | 4 | |
| Oleyl alcohol polyglycerolated with 4 mol of glycerol | 5.69 | AM |
| Oleic acid | 3 | |
| Oleyl amine comprising 2 mol of ethylene oxide sold under the commercial name Ethomeen O12 by the company Akzo | 7 | |
| Diethylaminopropyl laurylaminosuccinamate, sodium salt comprising 55% AM | 3.0 | AM |
| Oleyl alcohol | 5 | |
| Oleic acid diethanolamide | 12 | |
| Ethyl alcohol | 7 | |
| Propylene glycol | 3.5 | |
| Dipropylene glycol | 0.5 | |
| Propylene glycol monomethyl ether | 9 | |
| Ammonium acetate | 0.8 | |
| 20% aqueous ammonia of $NH_3$ (41.15% of $NH_4OH$) | 10 | |
| Demineralized water qs | 100 | g |

At the time of use, this composition was mixed weight for weight with the oxidizing agent 20V (comprising ≈80% of water) comprising a dispersion of fatty alcohols (8%) in water and 12% of hydrogen peroxide: PLATINIUM 20V. The pH of the mixture was 9.9±0.1.

Results

The emulsions A1 and A2 of the disclosure did not give off any disagreeable odor, unlike the composition of the comparative example. Furthermore, and as shown in the table below, the levels of lightening obtained with the emulsions of the disclosure were not significantly different from that obtained with the representative comparative example of the compositions of the prior art based on aqueous ammonia, which were known to give a good level of lightening.

|  | L* | a* | b* | ΔE |
|---|---|---|---|---|
| Untreated hair | 18.79 | 1.86 | 1.45 | / |
| Hair treated with emulsion A1 | 21.42 | 5.72 | 6.22 | 6.68 |
| Hair treated with emulsion A2 | 23.31 | 6.43 | 7.85 | 9.1 |
| Hair treated with the comparative composition | 22.1 | 6.11 | 6.97 | 7.71 |

What is claimed is:

1. A method for lightening keratin materials comprising applying a mixture to the keratin materials, wherein the mixture comprises:
   (A) a direct emulsion comprising:
      at least one non-silicone fatty substance other than fatty acids, chosen from compounds that are liquid at room temperature and at atmospheric pressure, and present in an amount greater than or equal to 50% by weight,
      at least one surfactant,
      at least one alkaline agent chosen from organic amines, organic amine salts, and ammonium salts, and
      an amount of water greater than 5% by weight, relative to the total weight of the emulsion; and
   (B) a composition comprising at least one oxidizing agent, and
   wherein the at least one non-silicone fatty substance is present in the mixture in an amount greater than 30%.

2. A method according to claim 1, wherein the water content in the emulsion (A) is greater than 10% by weight relative to the weight of the emulsion (A).

3. A method according to claim 1, wherein the water content in the emulsion (A) ranges from 10 to 50% by weight relative to the weight of the emulsion (A).

4. A method according to claim 1, wherein the at least one non-silicone fatty substance is chosen from alkanes of 6 to 16 carbon atoms, fatty alcohols, fatty acid esters, fatty alcohol esters, mineral oils of more than 16 carbon atoms, non-silicone plant, animal or synthetic oils, and non-silicone waxes.

5. A method according to claim 1, wherein the at least one non-silicone fatty substance content ranges from 50% to 80% by weight relative to the weight of the emulsion (A).

6. A method according to claim 1, wherein the at least one non-silicone fatty substance has a molecular weight greater than or equal to 360 g/mol.

7. A method according to claim 1, wherein the emulsion (A) comprises at least one nonionic surfactant.

8. A method according to claim 1, wherein the emulsion (A) comprises at least one nonionic surfactant chosen from monooxyalkylenated or polyoxyalkylenated, monoglycerolated or polyglycerolated nonionic surfactants.

9. A method according to claim 1, wherein the surfactant of the emulsion (A) is chosen from adducts of ethylene oxide with lauryl alcohol; adducts of ethylene oxide with cetearyl alcohol, adducts of ethylene oxide with cetyl alcohol; adducts of ethylene oxide with stearyl alcohol, adducts of ethylene oxide with isostearyl alcohol, adducts of ethylene oxide with lauric, palmitic, stearic or behenic acid, and mixtures thereof.

10. A method according to claim 1, wherein the organic amine is an alkanolamine or a basic amino acid.

11. A method according to claim 10, wherein
   the alkanolamine is chosen from 2-amino-2-methyl-1-propanol and monoethanolamine, or mixtures thereof, and
   the basic amino acid chosen from arginine, histidine, and lysine, or mixtures thereof.

12. A method according to claim 1, wherein the composition (B) comprises at least one oxidizing agent chosen from hydrogen peroxide, urea peroxide, alkali metal bromates or ferricyanides, and peroxygenated salts, and percarbonates.

13. A method according to claim 12, wherein the peroxygenated salt is chosen from alkali metal or alkaline-earth metal persulfates, perborates, and peracids and precursors thereof.

14. A method according to claim 1, wherein the composition (B) comprises more than 5% by weight of water relative to the weight of composition (B).

15. A method according to claim 1, wherein the composition (B) comprises more than 20% by weight of water relative to the weight of composition (B).

16. A method according to claim 1, wherein the mixture is obtained by extemporaneous mixing, at the time of use of the emulsion (A) and of the composition (B).

\* \* \* \* \*